United States Patent [19]
Andren

[11] 3,932,940
[45] Jan. 20, 1976

[54] DENTAL APPLIANCE
[76] Inventor: Frank J. Andren, 6889 Anthony Lane, Parma Heights, Ohio 44130
[22] Filed: Dec. 6, 1971
[21] Appl. No.: 204,900

[52] U.S. Cl................................................ 32/14 A
[51] Int. Cl.².......................................... A61C 7/00
[58] Field of Search..................... 32/16 A, 16 B, 71

[56] References Cited
UNITED STATES PATENTS

| | | | |
|---|---|---|---|
| 1,461,305 | 7/1923 | Brookes et al. | 32/10 R |
| 2,756,504 | 7/1956 | Levine | 32/71 |
| 2,958,945 | 11/1960 | Waldman | 32/14 A |
| 3,345,745 | 10/1967 | Muller | 32/14 A |

Primary Examiner—Robert Peshock
Attorney, Agent, or Firm—Bosworth, Sessions & McCoy

[57] ABSTRACT

A removably attachable orthodontic device for application to the face of a tooth and to which orthodontic apparatus may be secured and orthodontic forces applied to move and change the alignment of the tooth in the gum.

10 Claims, 3 Drawing Figures

INVENTOR.
FRANK J. ANDREN
BY Bosworth, Sessions,
Herrstrom & Cain
ATTORNEYS

DENTAL APPLIANCE

BACKGROUND OF THE INVENTION

This invention relates to orthodontic devices and, particularly, to means removably attachable to individual teeth permitting the application and transmission of applied forces to the teeth to urge them in one direction or another. In the past, it has been customary to band the individual teeth with soft tubular metallic material shaped generally to have a sliding fit over the tooth in question and to be cemented in place around the tooth. The bands are normally provided with suitable brackets attached to their outer surfaces for receiving and supporting arch wires passing over and along a row of teeth. The brackets may be shaped to accommodate and transmit forces applied by the wires in a desired direction and may include tabs or horns permitting the wires to be tied to the brackets and, thus, fastened to the bands and banded teeth.

Banding teeth to provide an anchorage or pad for or against which orthodontic force may be applied to the tooth has some disadvantages. It requires fashioning a sleeve or continuous band of soft metallic material to conform to the somewhat conical or tapered shape of a tooth. The front teeth, especially, generally have a substantially larger perimeter at their bases adjacent the gumline. The bands must be shaped to accommodate this difference in dimension. There is a natural tendency for the bands to slip off the teeth.

A further disadvantage to the orthodontic bands is that they require sufficient separation between the adjacent teeth to accommodate at least one and possibly two thicknesses of the banding material if adjacent teeth are both banded. Often, this requires stressing the teeth at relatively high levels in order to place the bands between them. Sometimes, teeth must be moved in some manner before the bands can be installed.

Finally, the banding material creates numerous and troublesome edges and even pockets in which material inimical to the health of the tooth enamel may collect.

BRIEF SUMMARY OF THE INVENTION

All the disadvantages of sleeves or bands employed in conventional orthodontic practice are overcome by this invention and the apparatus embodied in it. Briefly, the invention comprehends plates of suitable material upon which are fixedly mounted rests or brackets for receiving force-applying orthodontic apparatus such as arch wires. The plates are variously shaped to correspond generally to various tooth shapes. In the preferred embodiment, the plates are adapted, by a series of openings or perforations, to be firmly, yet easily, cemented onto a surface of the desired tooth. The conical or tapered shape of the teeth present no problem to the attachment of the plates. A space between adjacent teeth is not required to attach apparatus embodying this invention because no material is placed between adjacent teeth. Finally, the resulting combination of orthodontic apparatus is substantially, if not completely, free of edges and pockets for catching and detaining material deleterious to the tooth enamel. The plates comprehended by this invention are more easily applied and removed than the sleeve-type apparatus previously known so that superior results may be achieved with less effort and an economy of time advantageous to both dentist and patient.

DETAILED DESCRIPTION OF A PREFERRED EMBODIMENT

Figure 1:
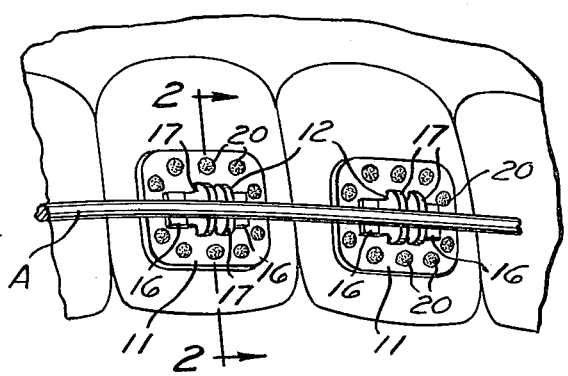
FIG. 1 is a perspective view of two preferred embodiments of the invention, one applied to each of two adjacent upper anterior teeth and together supporting a common arch wire.

As shown in the drawings, the preferred embodiment of the orthodontic device comprising this invention consists of a plate portion 11 and a bracket portion 12 fixedly mounted on the plate.

Plate portion 11 preferably consissts consists a thin, stiff piece of sheet material having oppositely facing plain surfaces. One surface is intended to generally match the surface of the tooth to which the device is to be mounted. The opposite surface of plate portion 11 faces away from the tooth and provides the mounting area for bracket portion 12. The material should be stiff enough to resist yielding in the face of forces encountered in orthodontic duty, yet bendable under sufficient pressure to be shaped prior to installation to conform to the contour of a tooth surface. The shape and area of the device preferably generally match the particular tooth face upon which the device is to be mounted.

Successful embodiments of this invention have comprised plates made of stainless steel sheet material 0.006 inch thick.

Figure 2:
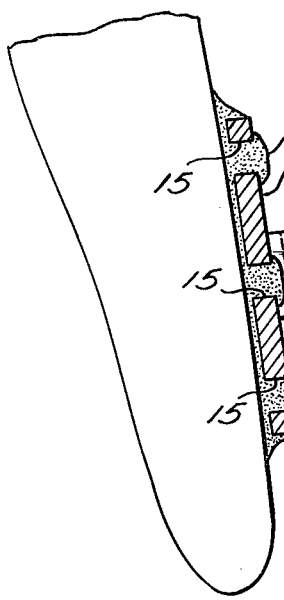
FIG 2 is a section through one of the devices shown in FIG. 1, taken in the plane of line 2—2.

The plate portion 11 is preferably provided with a plurality of openings extending between its oppositely facing plain surfaces. These openings appear clearly in FIG. 2. Openings 15 are preferably located in the marginal areas and spaced at least slightly away from the edge of plate 11. In addition, it is desirable to have at least one opening 15 generally centrally located in the plate. The purpose and advantage of the above-described openings will be explained below.

As mentioned above and shown in the drawings, plate portion 11 of the orthodontic device embodying this invention serves as the mounting plate and means for supporting and securing the bracket portion 12 to the tooth. Bracket portion 12 preferably consists of a base portion 16 and a projecting portion 17 joined to and extending outwardly from the base portion. Projecting portion 17 is provided with a saddle 18 for receiving cooperating orthodontic apparatus such as an arch wire A. Projecting portion 17 is also provided with a pair of horns 19 located on opposite sides of the saddle and for use in tying and securing arch wire A in saddle 18 and in force-applying relationship with bracket portion 12 of the device.

Figure 3:
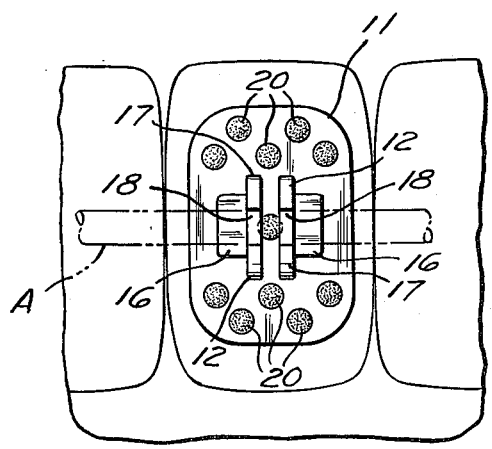
FIG. 3 is a front elevation view of a modified form of a preferred embodiment applied to the face of a lower anterior tooth and with an arch wire shown in phantom.

As shown most clearly in FIGS. 1 and 3, a pair of bracket portions 12 is preferably used in combination. Each bracket is fixedly mounted with its base portion 16 in engagement with the outwardly facing plain surface of plate portion 11. If brackets 12 are metal, for instance, they may be welded to plate portion 11. The pair of brackets 12 is preferably located on plate portion 11 with projecting portions 17 in a parallel spaced apart relationship and with the saddles 18 of the two projecting portions 17 in alignment for the support and receipt of a common arch wire. The use of two brackets 12 in spaced apart relationship enhances the directional control able to be imparted by the arch wire and transmitted to the tooth. Also, in the space between the pair of brackets 12, an opening can be provided, the advantage of which will appear below.

The devices embodying this invention are removably attached to their respective teeth by cementing them in the manner now to be described. First of all, the surface of the tooth to which the device is to be cemented is polished with pumice to remove any organic material. Next, the tooth enamel is etched with phosphoric acid, producing a matte finish when dry. Next, suitable cement such as carboxylate cement is applied to the prepared surface of the tooth and to the matching plain surface of plate 11. The cement will adhere to the surfaces involved, but is soft so that, when the plate portion is applied to the cement on the tooth, some of the cement is squeezed and extruded through openings 15 in the plate and flows outwardly over and onto the outwardly facing plain surface of the plate. After the plate has been properly positioned in this manner, it is allowed to stand undisturbed until the cement sets. In the case of carboxylate cement, this may be accomplished in about five minutes.

As is shown in the drawings, the device, when applied to the surface of a tooth in the manner described above, is held securely against the application of orthodontic forces by adhesion of the cement to the surface of plate portion 11 and the prepared surface of the tooth. In addition to this, the cement extends through openings 15 provided in plate portion 11 like fingers extending from the tooth surface. The fingers of cement are formed into buttons 20 after they have passed through openings 15 in plate portion 11 so that the cement extends over onto the outwardly facing plain surface on plate portion 11, further securing the device to the tooth and against motion relative to it.

Although, in the drawings, arch wire A is shown as merely resting in saddles 18 in the brackets of the devices shown, it will be readily apparent that the wire A may be tied in place by looping it back and forth between and around horns 19 of the individual projecting portions of brackets 12.

When the devices are no longer needed, they may be easily chipped from the tooth without any harm to the tooth. In the meantime, the device has provided a fixed means for applying orthodontic forces to the movement and/or correction of alignment of the tooth with adjacent teeth. The device does not require any space between adjacent teeth and presents no spaces into which unwanted material, i.e. food, etc., may accumulate. In fact, a fillet of cement may be provided around the edge of plate portion 11 and surfaces built that are free of sharpness and hiding places for food particles.

The openings 15 in plate portion 11 are provided in the marginal portion of the plate as shown in FIG. 1. A modified form of the preferred embodiment shown in FIG. 3 involves a plate portion somewhat taller than wide permitting a staggered double row of openings adjacent the upper and lower margins of the plate. The size and shape of the plate portion should generally match the surface area of the tooth to which it is to be applied and, in any event, should be no larger than the area so that it is not necessary for material to be extended into the space between adjacent teeth.

Openings 15 are preferably provided in the margins of plate 11 because this locates the extra holding power of the fingers of cement generally as far as possible from brackets 12 so they can most effectively resist tipping forces applied to plate 11 through brackets 12 by arch wire A. It is also desirable in order to preserve unimpaired adhesion to the tooth of the entire area of plate 11 to securely hold the central area of the plate as well as the marginal portions. This is nicely accomplished by locating at least a single opening 15 near the center of plate 11. The space between a pair of spaced apart brackets 12 is an advantageous place. This provides a holding finger of cement at the brackets. The brackets offer protection to the button at the end of the finger of cement.

Those skilled in the art will appreciate that various other changes and modifications can be made in the apparatus described herein without departing from the spirit and scope of the invention.

I claim:

1. An orthodontic device removably attachable to a tooth for cooperative connection with orthodontic apparatus and for transmitting a force applied by the connected apparatus to the tooth, said device comprising a thin plate of stiff, bendable sheet material having oppositely facing plain surfaces no larger than about the area of a tooth face, said bendable sheet material permitting said plate to be shaped generally to conform onen of said plain surfaces to a tooth surface, a bracket fixedly mounted on the other of said plain surfaces of said plate for receiving and supporting and for attachment to cooperating force-applying orthodontic apparatus, whereby suitable force is able to be effectively applied to a tooth through said device when said one of said plain surfaces of said plate is cemented to the tooth surface to which it generally conforms.

2. The device according to claim 1 in which said plate is provided with a plurality of openings extending between its said oppositely facing plain surfaces for permitting fingers of cement to extend from the tooth face through the plate and onto said other of said plain surfaces of the plate in aid of holding said plate to the tooth.

3. The device according to claim 2 in which said plurality of openings include openings through said plate adjacent its periphery.

4. The device according to claim 3 in which said plurality of openings include at least one opening located substantially centrally of said plate and closely adjacent said bracket.

5. The device according to claim 1 in which said bracket comprises a base portion adapted for overall engagement with said other of said plain surfaces of said plate and a projecting portion joined to and extending therefrom, said projecting portion having a saddle for receiving an arch wire and horns in aid of tying the arch wire into the saddle.

6. The device according to claim 1 together with a second bracket also fixedly mounted on said plate to form with said bracket a cooperating pair, each of the brackets of said pair having a saddle for receiving an arch wire and having horns in aid of tying the arch wire into the saddle, said pair of brackets being fixedly mounted with their saddles spaced apart and aligned for receiving and attachment to a common arch wire.

7. The device according to claim 1 together with a second bracket also fixedly mounted on said plate to form with said bracket a cooperating pair, each of the brackets of said pair comprising a base portion and a projecting portion joined to and extending therefrom, said projecting portion having a saddle for receiving an arch wire and horns in aid of tying the arch wire into the saddle and, said base portion having an area of surface larger than the area of junction with said projecting portion and adapted for overall engagement with said other of said plain surfaces of said plate, said pair of brackets being fixedly mounted with their projecting portions spaced apart and their saddles aligned for receiving and attachment to a common arch wire.

8. The device according to claim 2 in which said bracket comprises a base portion and a projecting portion joined to and extending therefrom, said projecting portion having a saddle for receiving an arch wire and having horns in aid of tying the arch wire into the saddle, and said base portion having an area of surface larger than the area of junction with said projecting portion and adapted for overall engagement with an area of said other of said plain surfaces of said plate free of said openings.

9. The device according to claim 2 together with a second bracket also fixedly mounted on said plate to form with said bracket a cooperating pair, each of the brackets of said pair having a saddle for receiving an arch wire and having horns in aid of tying the arch wire into the saddle, said pair of brackets being fixedly mounted with their saddles spaced apart and aligned for receiving and attachment to a common arch wire.

10. The device according to claim 9 in which said brackets are spaced apart at least the diameter of one of said openings, one of said openings in said plate opening into the space between said brackets.

* * * * *